(12) United States Patent
Gobbi

(10) Patent No.: US 7,705,051 B2
(45) Date of Patent: Apr. 27, 2010

(54) THERAPEUTICAL AGENT USEFUL FOR THE TREATMENT OF PLASMA CELL NEOPLASIAS

(75) Inventor: Rosa Gobbi, Sion (CH)

(73) Assignee: Eureon AG, Freiburg (DE)

( * ) Notice: Subject to any disclaimer, the term of this patent is extended or adjusted under 35 U.S.C. 154(b) by 413 days.

(21) Appl. No.: 11/663,553

(22) PCT Filed: Sep. 20, 2005

(86) PCT No.: PCT/EP2005/010135

§ 371 (c)(1), (2), (4) Date: May 21, 2007

(87) PCT Pub. No.: WO2006/032458

PCT Pub. Date: Mar. 30, 2006

(65) Prior Publication Data

US 2009/0203939 A1      Aug. 13, 2009

(30) Foreign Application Priority Data

Sep. 24, 2004   (IT)   .................. MI2004A1822

(51) Int. Cl.
 *A61K 31/185* (2006.01)
(52) U.S. Cl. .................................................. 514/578
(58) Field of Classification Search .................. None
 See application file for complete search history.

(56) References Cited

U.S. PATENT DOCUMENTS 4,372,894 A * 2/1983 Helgstrand et al. .......... 558/181
2004/0180956 A1 * 9/2004 Bartorelli .................... 514/557

FOREIGN PATENT DOCUMENTS

WO   WO 03/006031    1/2003
WO   WO 2005/097084  10/2005

* cited by examiner

*Primary Examiner*—Paul A Zucker
(74) *Attorney, Agent, or Firm*—Young & Thompson

(57) ABSTRACT

The use of calcium trifluoroacetate for the preparation of a drug for the treatment of plasma cell neoplasias, particularly multiple myeloma.

5 Claims, No Drawings

THERAPEUTICAL AGENT USEFUL FOR THE TREATMENT OF PLASMA CELL NEOPLASIAS

The present invention relates to the use of calcium trifluoroacetate for the preparation of a medicament for the treatment of plasma cell neoplasias, in particular multiple myeloma.

Calcium trifluoroacetate was recently studied as a cytotoxic drug against cell lines of solid tumors of various origin (colon, lung, pancreas, breast, prostate, liver, stomach and ovary). Preliminary clinical evidence proved that calcium trifluoroacetate is well tolerated and substantially free from important toxic effects when administered subcutaneously or intravenously to patients with colon or breast carcinomas. The therapeutical results, although preliminary, have been surprising in terms of reduction in tumor mass, reduction or disappearance of ascitis and metastatic nodules and reduction in tumor markers (CA19.9 and alpha-foetoproteins).

Plasma cell neoplasias are a group of clinically and biologically heterogeneous diseases, characterized by hyperproliferation of an immunoglobulin-producing cell clone and hence by the presence of immunoglobulins or monoclonal fragments thereof in blood and urines. Among plasma cell neoplasias, multiple myeloma, also known as plasma cell myeloma or myelomatosis, is undoubtedly a particularly serious disease for which no available effective therapeutical protocols exist.

Multiple myeloma is in fact a neoplastic process with usually poor prognosis, characterized by bone marrow plasma cell infiltration and production of monoclonal immunoglobulins type G, A, D or E or Bence Jones proteins ($\kappa$ or $\lambda$ subunits).

Patients with this disease often suffer bone lesions, anemia, renal damage, hypercalcemia and immunodepression. The chemotherapy treatment with conventional alkylating agents such as cyclophosphamide and melfalan, optionally combined with prednisone, increases the patients mean survival which however is still of only 2-3 years in the more favourable cases and involves severe side effects, mainly on blood crasis (leukopenia and plastocytopenia).

It has now been found that calcium trifluoroacetate has surprising cytotoxic activity not only on solid tumors cell lines, but also on multiple myeloma, chronic and acute myeloid leukemia human cell lines, while being devoid of toxicity on marrow mononuclear cells (LD-MNC) and $CD34^+$ stem cells of bone marrow from healthy volunteers. This selectivity towards myeloma and leukemia cells is surprising and induces markedly more favourable therapeutic index than known alkylating agents, which are cytotoxic also on non neoplastic cells.

The activity of calcium trifluoroacetate was evaluated in vitro, as reported in the following examples, on collection cell lines (ATCC, National Cancer Institute, DSMZ), widely used in cytotoxicity studies. In vivo preliminary evidence in dogs is also available. Multiple myeloma is in fact a disease also diffused in animals, particularly in dogs, with characteristics superimposable to the human disease. The therapeutical activity in dogs is therefore highly predictive for the therapeutical activity in human clinics.

For the envisaged therapeutical uses, calcium trifluoroacetate will be administered through the parenteral route, in particular intramuscularly, subcutaneously or intravenously, at dosages ranging from 20 to 200 mg/kg/day, preferably from 20 to 100 mg/kg/day intravenously. The treatment, thanks to its poor toxicity, can be protracted for the time necessary to obtain the improvement or resolution of the pathologic condition.

Calcium trifluoroacetate, if desired, can be administered in combination with other therapeutical agents already used in chemotherapy protocols for multiple myeloma.

In addition to multiple myeloma, the plasma cell neoplasias that can be treated with calcium trifluoroacetate comprise macroglobulinemia, systemic primitive amyloidosis and heavy chain diseases.

As mentioned above, calcium trifluoroacetate can also be used in the veterinary field, in particular for the treatment of multiple myeloma in dogs. For this purpose, the invention yields veterinary compositions comprising calcium trifluoroacetate as the active ingredient in admixture with a suitable carrier for the parenteral administration, such as sterile apyrogenic water or physiological solution for the intravenous administration.

The invention is illustrated in greater detail by the following example.

EXAMPLE

Effect of $Ca(CF_3COO)_2$ on Multiple Myeloma, Chronic and Acute Myeloid Leukemia Human Cell Lines and Human Marrow Stem Cells Cytotoxicity of $Ca(CF_3COO)_2$ was evaluated on ten multiple myeloma human cell lines (RPMI8226, IM9, SULTAN, ARH77, KMS12, KMS26, KMS34, H929 and U266), two chronic myeloid leukemia human cell lines (K562 and AR230), one acute myeloid leukemia human cell line (KG1a), medullary mononuclear cells (LD-MNC) and $CD34^+$ human bone marrow stem cells.

A cytotoxicity test based on the cleavage of tetrazolium salts by mitochondrial dehydrogenase in viable cells (WST-1) was used.

All of the multiple myeloma cell lines and human marrow cells were cultured in Iscove's Modified Dulbecco medium with 10% bovine calf serum (FBS): chronic and acute myeloid leukemia cells were cultured in RPMI 1640 medium with 10% FBS. Bone marrow samples from 2 healthy donors were separated on a Ficoll density gradient. Part of the separated cells (LD-MNC) in a case were incubated with immunomagnetic particles (Miltenyi Biotec) conjugated with the antibody anti-CD34 antigene and afterwards were separated on immunomagnetic columns.

10,000 cells per 96 wells were plated in 100 μl of Iscove's Modified Dulbecco culture medium with 10% foetal serum. 20 μl of $Ca(CF_3COO)_2$ at the concentrations of 100, 50, 37.5, 25, 15, 12.5, 10 and 6.25 mg/ml were then added. After incubation at 37° C. and 5% $CO_2$ under humid atmosphere overnight, 10 μl/well of WST-1 was added and after 4 hours at 37° C. and 5% $CO_2$ under humid atmosphere, the plate was read with a 1420 VICTOR multilabel counter, EG&G Wallac, at 560 nm and 690 nm. Each sample was plated in triplicate and toxicity was evaluated as the ratio of the mean absorbance value of three triplicates treated with $Ca(CF_3COO)_2$ scalar doses to the mean absorbance value of three untreated control triplicates:

$$1 - \frac{\text{Treated cells absorbance}}{\text{Untreated cells (control) absorbance}} \times 100 = \% \text{ dead cells}$$

$Ca(CF_3COO)_2$ turned out particularly toxic also at lower doses on chronic myeloid leukemia lines (K562 and AR230).

Acute myeloid leukemia line KG1a is sensitive to $Ca(CF_3COO)_2$ only at higher doses.

All multiple myeloma cell lines, with the exception of KMS27, are sensitive to $Ca(CF_3COO)_2$: in particular, cell lines with slower growth (H929 and U266) appeared less sensitive to low doses of $Ca(CF_3COO)_2$ compared with those with more rapid growth (RPMI8226, IM9, SUTAN, ARH77, KMS12, KMS26, KMS34).

$Ca(CF_3COO)_2$ is not toxic for human LD-MNC from healthy donors also at higher doses, whereas stem cells $CD34^+$ are slightly sensitive to $Ca(CF_3COO)_2$.

Results are reported in the following Table.

| Conc. | LD-MNC | CD34+ | AR230 | K562 | KG1a | RPMI8826 | IM9 |
|---|---|---|---|---|---|---|---|
| 125 | 0 | 0 | 11 | 29 | 2 | 12 | 0 |
| 200 | 0.4 | 16 | 51 | 63 | 0 | 38 | 17 |
| 250 | 0.4 | 10 | 40 | 58 | 0 | 33 | 9 |
| 300 | 0.3 | 21 | 44 | 65 | 0 | 34 | 14 |
| 500 | 0.2 | 12 | 58 | 52 | 0 | 43 | 32 |
| 750 | 0.2 | 9 | 69 | 63 | 6 | 53 | 35 |
| 1000 | 0.1 | 24 | 73 | 64 | 11 | 61 | 50 |
| 2000 | 1 | 18 | 78 | 72 | 40 | 98 | 100 |

| Conc. | SULTAN | ARH77 | KMS12 | KMS26 | KMS27 | KMS34 | H929 | U266 |
|---|---|---|---|---|---|---|---|---|
| 125 | 0 | 0 | 0 | 0 | 0 | 20 | 0 | 0 |
| 200 | 1 | 2 | 39 | 0 | 4 | 20 | 0 | 0 |
| 250 | 3 | 10 | 53 | 5 | 0 | 1 | 0 | 0 |
| 300 | 10 | 12 | 52 | 33 | 0 | 6 | 0 | 0 |
| 500 | 11 | 32 | 79 | 49 | 0 | 7 | 0 | 0 |
| 750 | 20 | 19 | 75 | 32 | 0 | 36 | 18 | 3 |
| 1000 | 32 | 31 | 80 | 33 | 0 | 49 | 68 | 39 |
| 2000 | 69 | 90 | 100 | 100 | 0 | 100 | 100 | 100 |

The invention claimed is:

1. A method of treating plasma cell neoplasia in a subject, comprising administering an effective amount of calcium trifluoroacetate to the subject.

2. The method of claim 1, wherein the plasma cell neoplasia is multiple myeloma, chronic myeloid leukemia or acute myeloid leukemia.

3. The method of claim 1, wherein the effective amount of calcium trifluoroacetate is 20 to 200 mg/kg/day.

4. The method of claim 1, wherein the trifluoroacetate is administered intramuscularly, subcutaneously, or intravaneously.

5. The method of claim 1, wherein the calcium trifluoroacetate is administered in combination with an effective amount of at least one other chemotherapeutic agent.

* * * * *